(12) United States Patent
Hoernig

(10) Patent No.: US 7,484,889 B2
(45) Date of Patent: Feb. 3, 2009

(54) X-RAY APPLIANCE WITH A ROTATING FLAT DETECTOR

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 138 days.

(21) Appl. No.: 11/283,687

(22) Filed: Nov. 22, 2005

(65) Prior Publication Data

US 2006/0126797 A1   Jun. 15, 2006

(30) Foreign Application Priority Data

Nov. 25, 2004   (DE) ................ 10 2004 057 003

(51) Int. Cl.
  *G01D 18/00* (2006.01)
(52) U.S. Cl. .................. 378/207; 250/252.1
(58) Field of Classification Search ............. 378/207; 250/252.1, 363.09; 382/132
  See application file for complete search history.

(56) References Cited

U.S. PATENT DOCUMENTS

| | | | |
|---|---|---|---|
| 4,578,806 A | 3/1986 | Grass et al. | |
| 4,736,399 A | 4/1988 | Okazaki | |
| 6,379,043 B1 | 4/2002 | Zylka et al. | |
| 6,704,388 B2 | 3/2004 | Op De Beek et al. | |
| 6,811,313 B2 * | 11/2004 | Graumann et al. | .......... 378/196 |
| 7,026,608 B2 | 4/2006 | Hirai | |
| 2003/0007601 A1 | 1/2003 | Jaffray et al. | |

FOREIGN PATENT DOCUMENTS

| | | |
|---|---|---|
| DE | 19856536 A1 | 6/2000 |
| EP | 1349378 A1 | 10/2003 |
| WO | WO-02/36012 A1 | 5/2002 |

\* cited by examiner

*Primary Examiner*—Jurie Yun
(74) *Attorney, Agent, or Firm*—Harness, Dickey & Pierce PLC

(57) ABSTRACT

An X-ray appliance is disclosed including an X-ray emitter, arranged such that it cannot rotate, and a flat detector mounted such that it can rotate. The appliance further includes an upgraded calibration device, by which calibration images are recorded for different rotations of the detector relative to the X-ray emitter, with a complete calibration data record with a gain image and pixel defect map being created for each rotation position of the flat detector.

12 Claims, 1 Drawing Sheet

X-RAY APPLIANCE WITH A ROTATING FLAT DETECTOR

The present application hereby claims priority under 35 U.S.C. §119 on German patent application number DE 10 2004 057 003.5 filed Nov. 25, 2004, the entire contents of which is hereby incorporated herein by reference.

FIELD

The invention generally relates to an X-ray appliance having an X-ray emitter, which is arranged such that it cannot rotate, and having a flat detector which is mounted such that it can rotate.

BACKGROUND

Very widely differing embodiments of flat detectors are used as X-ray detectors, inter alia in medicine. The purpose of the different sizes and formats, in particular the rectangular shape, is, for example, optimized patient access and matching to the respective examination area (for example in cardiology, angiography and radiography).

In many X-ray appliances, it is possible to rotate the detector, as is the case by way of example on each C arc, in order to use the detector to optimally display the image area to be examined and/or the image format in conjunction with the respective angulation. For example, detectors with a rectangular usable image format, which are used for specific multifunctional applications, are frequently rotated through 90° during the examination.

Non-square detectors, in particular, are subject to the problem that the correction images that are used from the calibration were acquired with the detector in only one fixed position with respect to the X-ray tube. This results in reduced image quality or image artifacts, caused by the different position of the detector relative to the tube (including heeling effect, shadowing, different pixel sensitivity in the detector edge areas).

Finally, the above effects such as shadowing in edge and corner regions of the detector can lead to increased spurious pixel defect identification in those areas.

SUMMARY

At least one embodiment of the invention includes an object of refining an X-ray appliance such that no changes can occur and, in particular, little or no deterioration can occur in the image display as a result of rotation of the flat detector.

In order to achieve this object, an X-ray appliance such as this is, according to at least one embodiment of the invention, including an upgraded calibration device, by which calibration images are recorded for different rotations of the detector relative to the X-ray emitter, with a complete calibration data record with a gain image and pixel defect map being created for each rotation position of the flat detector.

The upgraded calibration device according to at least one embodiment of the invention allows the X-ray images to be corrected for each flat detector's rotation that is desired and selected by the doctor, with the calibration image with the closest rotation in each case being used for correction of an X-ray image.

In general, it cannot be assumed that there will be one calibration image precisely for the recording angle when a plurality of calibration images are recorded over a rotation angle of 90°, which could have been selected by the doctor in that specific case on the basis of the specific characteristics. The calibration image of the closest rotation angle is used in these cases, in which case it can be assumed that the changes during rotation of the flat image detector do not in fact occur suddenly.

In this case, in a refinement of at least one embodiment of the invention, it has been found to be particularly advantageous to use an averaged calibration image of the closest rotation values in both directions in each case for correction of an X-ray image. For example, if it is therefore assumed that an X-ray image is recorded with a rotation of 40°, while calibration images are available only for rotation angles of 15°, 30°, 45° etc., then an average calibration image from the recordings at 30° and at 45° can be used for correction purposes, with appropriate weighting.

BRIEF DESCRIPTION OF THE DRAWINGS

Further advantages, features and details of the invention will become evident from the following description of one example embodiment, and from the drawings, in which.

DETAILED DESCRIPTION OF THE EXAMPLE EMBODIMENTS

Figure 1:
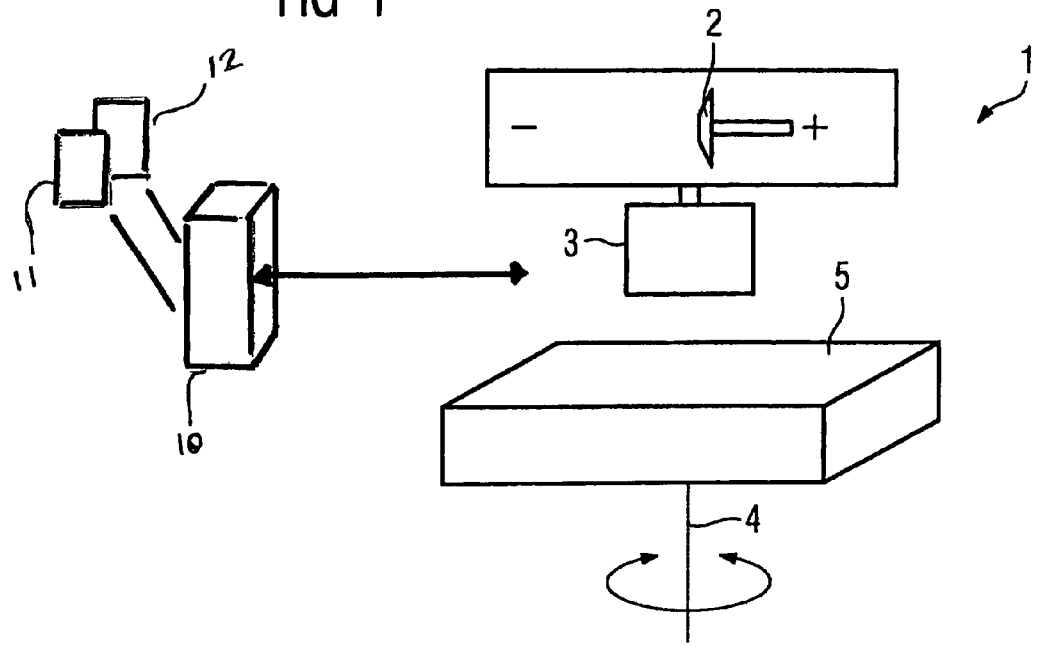
FIG. 1 shows a schematic illustration of an X-ray emitter and of a flat image detector, illustrated in distorted perspective form.
Figure 2:
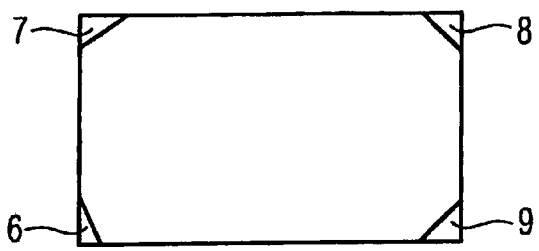
FIGS. 2 and 3 show calibration images in different rotation positions of the flat detector with respect to the non-rotating X-ray emitter, with image artifacts being shown only schematically in the corners, while pixel changes in the rest of the image area are not illustrated.
Figure 3:
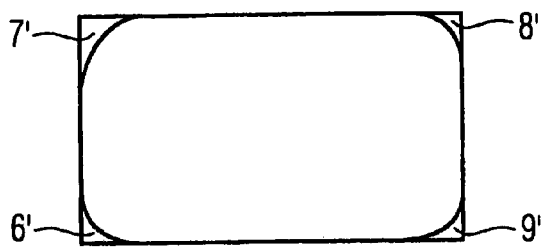

At 1, FIG. 1 schematically shows an X-ray emitter with a rotating anode 2 and an aperture system 3, which is arranged above a flat detector 5 that is mounted such that it can rotate about its central axis of symmetry 4. When an image is being recorded, image artifacts 6 to 9 occur in the corners, with a different appearance in the different rotation positions of the flat detector with respect to the X-ray emitter, which does not rotate at the same time, as is shown in FIGS. 2 and 3. The corresponding artifacts in the corners are annotated 6' to 9' in FIG. 3.

In addition to these artifacts, there are also different pixel values in the image of course, with the relationships being otherwise unchanged, that is to say the same X-ray emitter, or an X-ray emitter operated in the same way, and the same object between the X-ray emitter and the flat detector, and these do not actually originate from the structure to be imaged but are caused only by the asymmetries and, for example, the heeling effect, shadowing and different pixel sensitivity in the detector edge areas.

According to at least one embodiment of the invention, calibration images are created for this reason for a plurality of different rotations, that is to say rotated angular positions of the flat detector 5, and these can each be used for correction of an X-ray image in a rotation position that is desired by the doctor. The calibration recordings should be carried out at least in 45° steps, but preferably in smaller angular steps, with the magnitude of the angular steps for calibration image acquisition being selected as follows: the larger the detector and the poorer the ratio of the width and length, the more calibration steps are required. Depending on the detector rotation in each case selected by the doctor, the system records this angle and selects a matching data set from the calibration and uses this in the correction of the pipeline in the system. For example, a calibration device 10, by which calibration images are recorded for different rotations of the detector 5 relative to the X-ray emitter 1, may create a complete calibration data record with a gain image 11 and a pixel defect map 12 for each rotation position of the flat detector.

The proposed measures make it possible to entirely prevent or considerably reduce the loss of image quality described initially in digital X-ray systems with rotating flat detectors. Furthermore, it is possible to prevent pixels from the detector matrix which are located in critical areas such as the detector corners being recorded in the defect map, and possibly leading to a failure of the detector. This saves increased maintenance action and unnecessary detector replacement.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray appliance, comprising:
    an X-ray emitter, arranged such that it cannot rotate;
    a flat detector, mounted to be rotatable in a plane about a central axis of the flat detector; and
    a calibration device, by which calibration images are recorded for different rotations of the detector relative to the X-ray emitter, with a complete calibration data record with a gain image and pixel defect map being created for each rotation position of the flat detector.

2. The X-ray appliance as claimed in claim 1, wherein the calibration image with the relatively closest rotation to a rotation of an X-ray image is used for correction of the X-ray image.

3. The X-ray appliance as claimed in claim 1, wherein an averaged calibration image from the relatively closest rotation in both directions to a rotation of an X-ray image is used for correction of the X-ray image.

4. The X-ray appliance as claimed in claim 2, wherein an averaged calibration image from the relatively closest rotation in both directions to the rotation of the X-ray image is used for correction of the X-ray image.

5. An X-ray appliance, comprising:
    a non-rotatable X-ray emitter;
    a rotatable flat detector rotatable in a plane about a central axis of the flat detector; and
    a calibration device, to record a calibration image for a rotation of the detector relative to the X-ray emitter, a calibration data record including a gain image and pixel defect map being created for multiple rotation positions of the flat detector.

6. The X-ray appliance as claimed in claim 5, wherein the calibration image with the relatively closest rotation to a rotation of an X-ray image is used for correction of the X-ray image.

7. The X-ray appliance as claimed in claim 5, wherein an averaged calibration image from the relatively closest rotation in both directions to a rotation of an X-ray image is used for correction of the X-ray image.

8. The X-ray appliance as claimed in claim 6, wherein an averaged calibration image from the relatively closest rotation in both directions to the rotation of the X-ray image is used for correction of the X-ray image.

9. An X-ray appliance, comprising:
    a non-rotatable X-ray emitter;
    a rotatable flat detector rotatable in a plane about a central axis of the flat detector; and
    means for recording a calibration image for a rotation of the detector relative to the X-ray emitter, a calibration data record including a gain image and pixel defect map being created for multiple rotation positions of the flat detector.

10. The X-ray appliance as claimed in claim 9, wherein the calibration image with the relatively closest rotation to a rotation of an X-ray image is used for correction of the X-ray image.

11. The X-ray appliance as claimed in claim 9, wherein an averaged calibration image from the relatively closest rotation in both directions to a rotation of an X-ray image is used for correction of the X-ray image.

12. The X-ray appliance as claimed in claim 10, wherein an averaged calibration image from the relatively closest rotation in both directions to the rotation of the X-ray image is used for correction of the X-ray image.

* * * * *